United States Patent [19]

Youssefyeh

[11] Patent Number: 4,576,942
[45] Date of Patent: Mar. 18, 1986

[54] ANTI-ALLERGIC AND ANTI-INFLAMMATORY BI- AND TRI-CYCLO-1,4-THIAZINE DERIVATIVES, COMPOSITION, AND METHOD OF USE THEREFOR

[75] Inventor: Raymond D. Youssefyeh, Tarrytown, N.Y.

[73] Assignee: USV Pharmaceutical Corp., Tarrytown, N.Y.

[21] Appl. No.: 630,048

[22] Filed: Jul. 12, 1984

[51] Int. Cl.$^4$ .................. A61K 31/38; A61K 31/54; C07D 279/16; C07D 513/02
[52] U.S. Cl. .................. 514/222; 514/225; 544/32; 544/34; 544/51; 544/52; 544/48
[58] Field of Search ............ 544/32, 34, 48, 51, 544/52; 424/246; 514/222, 225

[56] References Cited

U.S. PATENT DOCUMENTS 4,031,087  6/1977  Powell .................. 424/246

Primary Examiner—Henry R. Jiles
Assistant Examiner—J. G. Mullins

[57] ABSTRACT

Compounds of the formulae

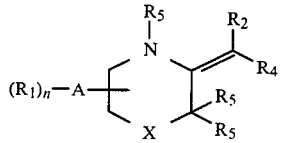

I

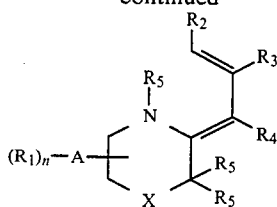

II

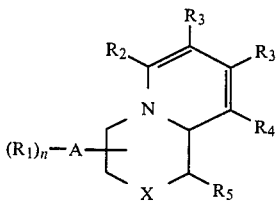

III wherein,
A is benzo, pyrido, thieno, pyrazolo, imidazo, pyrimido, isoxazolo, thiazolo, furo or pyrrolo;
X is O, S, SO or $SO_2$;
$R_1$ is H, alkyl, aryl, OH, OR, aryloxy, halogen, amino, nitro, cyano, COOR, trihalomethyl,

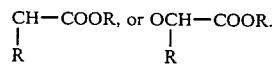

$R_2$, $R_3$, $R_4$ and $R_5$ are identical or different and each represent H, alkyl, aryl, OH, OR, amino, alkylamino, dialkylamino, COOR, thio, alkylthio, cyano, or halogen; and n is 1-2; and pharmaceutically acceptable salts thereof having anti-allergy and anti-inflammatory activity.

5 Claims, No Drawings

ANTI-ALLERGIC AND ANTI-INFLAMMATORY BI- AND TRI- CYCLO-1,4-THIAZINE DERIVATIVES, COMPOSITION, AND METHOD OF USE THEREFOR

This invention relates to new pharmaceutically active compounds and more particularly to certain new thiazines possessing useful pharmacologic activities, especially regulating the activity of lipoxygenase and as such possess therapeutic value in the treatment of inflammatory conditions and allergic responses such as anaphylaxis and asthma.

The new compounds of the present invention have the formulae:

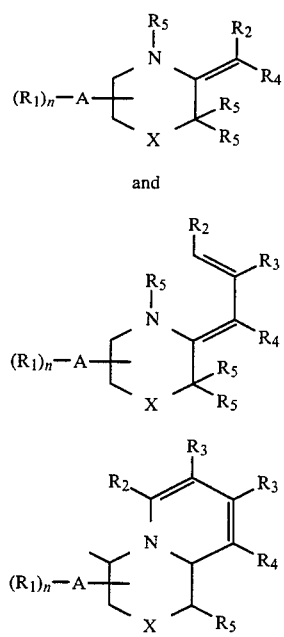

and pharmaceutically acceptable salts thereof, wherein,

A is benzo, pyrido, thieno, pyrazolo, imidazo, pyrimido, isoxazolo, thiazolo, furo or pyrrolo;

X is O, S, SO or $SO_2$;

$R_1$ is H, alkyl, aryl, OH, OR, aryloxy, halogen, amino, nitro, cyano, COOR, trihalomethyl,

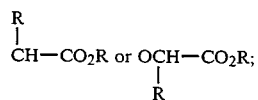

$R_2$, $R_3$, $R_4$ and $R_5$ are identical or different and each represent H, alkyl, aryl, OH, OR, amino, alkylamino, cyano, dialkylamino, COOR, thio, alkylthio, or halogen; and n is 1–2.

Unless expressly indicated otherwise herein, alkyl represents straight-chain, branched or cyclic alkyl with up to 10 carbon atoms, in particular straight-chain or branched alkyl with up to 6 carbon atoms; aryl preferably denotes phenyl or naphthyl; R in OR and COOR denotes lower-alkyl having 1–6 carbon atoms; and halogen preferably denotes Cl, F and Br.

The present new compounds are readily preparable by art-recognized procedures.

A schematic procedure, using commercially available starting materials (such as starting materials from Aldrich Chemical Co. and Lonzo Chemical Co.) is illustrative of procedures leading to the synthesis of compounds of the present invention.

Typical Synthesis

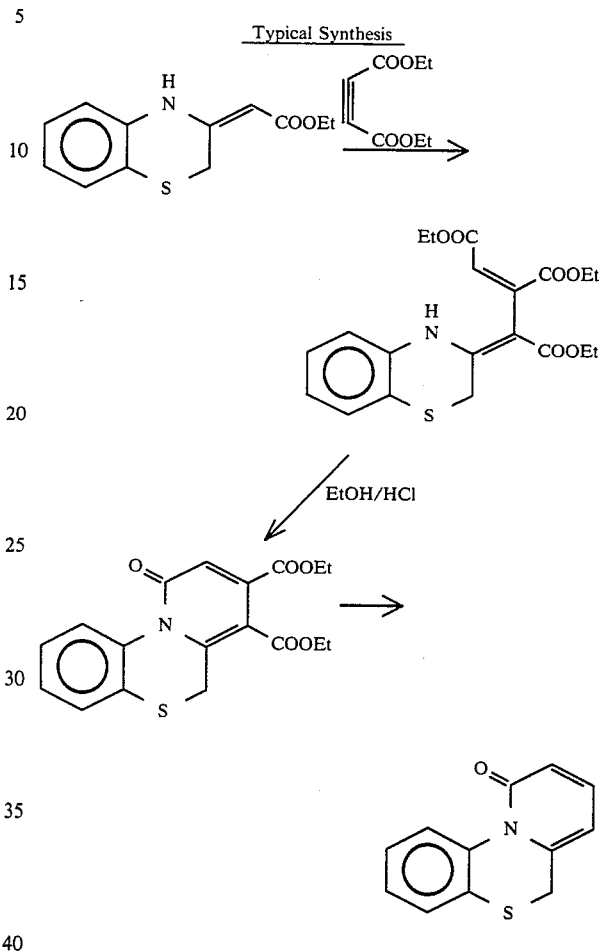

Compounds of the present invention were found to be effective anti-inflammatory and anti-allergic agents.

In general, the substance of this invention is administered in analogy to known, commercially available formulations with a similar indication in dosages of approximately 1 to 200 mg per dosage unit or higher. The daily dosage is approximately 0.02–5 mg/kg of body weight. It is to be understood, however, that the particular dose for each patient as usual depends on very diverse factors, such as the age, body weight, general condition of health, sex, diet, and the like of the patient, on the time and route of administration, on the rate of excretion, on the combination of medicaments and on the severity of the particular disease to which therapy relates.

The compounds of the present invention may be administered enterally, parenterally or topically. The compound may be incorporated into pharmaceutical formulations having excipients suitable for these administrations and which do not adversely react with the compounds, for example, water, vegetable oils, certain alcohols and carbohydrates, gelatin, magnesium stearate, talc, cornstarch or petroleum jelly. The pharmaceutical formulations containing an active compound of the present invention may be made into: tablets, capsules, elixirs, drops or suppositories for enteral administration; solutions, suspensions or emulsions for parenteral administration; ointments, creams or powders for topical application, and inhalation capsules, sprays, nasal and eye drops.

The following examples will further illustrate the invention.

EXAMPLE 1

Ethyl-2-[1,3-dihydro-(1,4)-benzothiazine-2-ilidene]acetate

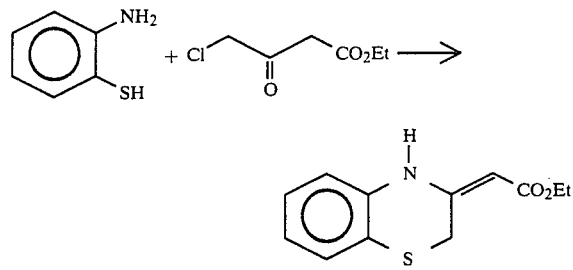

To a mixture of 134 g sodium bicarbonate in 480 ml of water and 480 ml isopropanol was added 200 g of 2-aminothiophenol (Aldrich Chemical Co.) and stirring was continued at 60° C. for ½ hr. 263 g of ethyl-4-chloroacetoacetate was then added and stirring was continued at 80° C. for 1 hr. The reaction mixture was then diluted with 480 ml H$_2$O, cooled in ice-bath, filtered and washed with water giving 473 g crude solid which was crystallized from ethanol to give 331 g of ethyl-2-[1,3-dihydro(1,4)-benzothiazine-2-ilidene]acetate, mp 67°-9° C.

EXAMPLE 2

Ethyl-2-[1,3-dihydro-pyrido[2,3-b][1,4]thiazine-2-ilidene]acetate

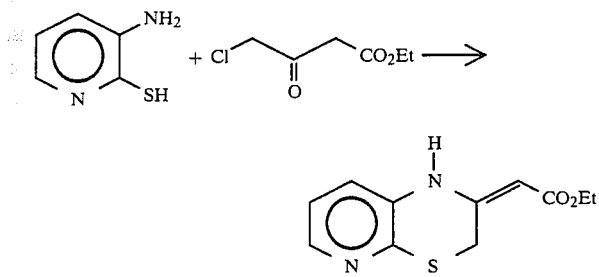

To a mixture of 5 g sodium bicarbonate in 100 ml isopropanol and 100 ml water was first added 7.5 g 3-amino-2-mercaptopyridine and then 10 g ethyl-4-chloroacetoacetate and stirring was continued at 70° C. for 1 hr. It was cooled, poured on ice-water and filtered. The solid precipitate was filtered, washed with water and dried giving 9.4 g crude product which was crystallized from EtOAc/hexane m.p. 90°-91° C.

EXAMPLE 3

N-Phenyl-2[1,3 dihydro-[1,4]benzothiazine-2-ilidene]acetamide

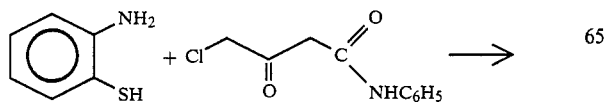

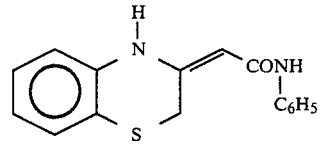

To a mixture of 17 g of NaHCO$_3$ in 100 ml water and 200 ml isopropanol was first added 25 g of 2-aminothiophenol (Aldrich Chemical Co.,) and then 39 g of 4-chloro-N-phenylacetoacetamide (Lonzo Chemical Co.). Stirring at R.T. was continued for 3 hrs. It was diluted with water, filtered, and the precipitate washed with water. The crude solid, 44.5 g, was crystallized from EtOAc/hexane, m.p. 153°-4° C.

EXAMPLE 4

N-2-chlorophenyl-2-[1,3-dihydro-[1,4]-benzothiazine-2-ilidene]acetamide

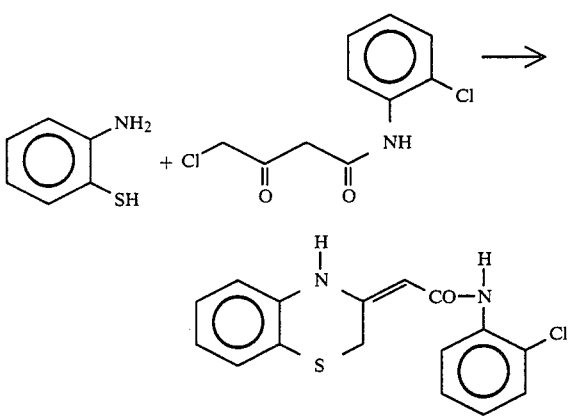

To a cold mixture of 17 g NaHCO$_3$ in 100 ml water and 200 ml isopropanol was added first 25 g 2-aminothiophenol and then 46 g 4-chloro-N-[2-chlorophenyl-]acetoacetamide. Stirring was continued for 3 hrs. It was diluted with water and filtered. The crude solid, 49.3 g, was crystallized from EtOAc/hexane, m.p. 124°-6° C.

EXAMPLE 5

Diethyl-4-[1,3-dihydro(1,4)-benzothiazine-2-ilidene]-3-carbethoxy-2-ene-glutarate

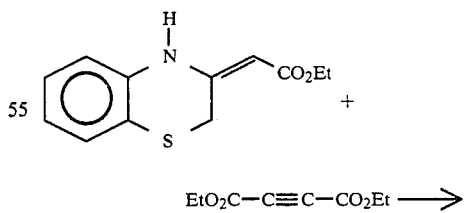

+

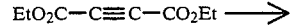

EtO$_2$C—C≡C—CO$_2$Et ⟶

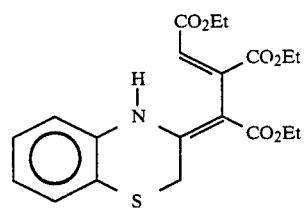

To a solution of 15 g of ethyl-2-[1,3-dihydro(1,4)-benzothiazine-2-ilidene]acetate in 3.8 g glacial acetic acid and 150 ml ethanol was added 10.8 g diethyl acetylenedicarboxylate and stirring was continued for two days. Solvent was removed and the oily residue was purified by HPLC using 10% EtOAc/hexane as eluent. Crystallization of the second fraction from EtOH gave 12.8 g of the expected product, m.p. 81°-2° C.

EXAMPLE 6

Ethyl-N-phenyl-4-[1,3-dihydro-(1,4)-benzothiazine-2-ilidene]-3-carbethoxy-2-ene glutaramide

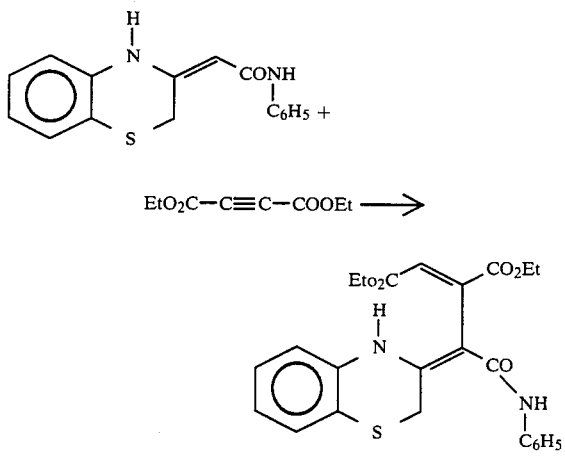

A mixture of 5.6 g N-phenyl-2[1,3-dihydro-(1,4)-benzothiazine-2-ilidene]acetamide, 4 g diethyl acetylenedicarboxylate, 1.4 ml glacial HOAC in 100 ml ethanol was stirred at 60° C. for 4 hrs. It was evaporated to dryness, dissolved in ether and precipitated by addition of hexane. After filtration, the crude solid product was recrystallized from ether/hexane to give 2.1 g of pure product, m.p. 100°-2° C.

EXAMPLE 7

Diethyl-2-[1,3-dihydro-(1,4)benzothiazine-2-ilidene]-3-oxo-succinate

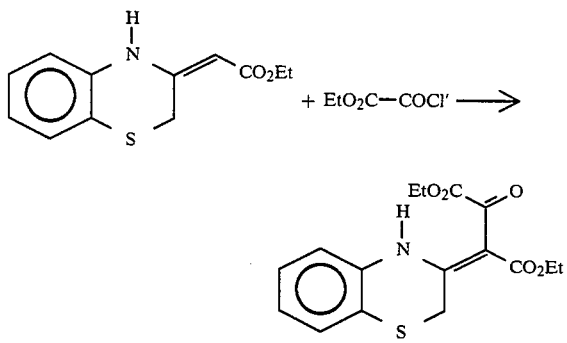

A mixture of 23.5 g of ethyl-2-[1,3-dihydro-(1,4)-benzothiazine-2-ilidene]acetate, 14 g ethyl oxalyl chloride in 200 ml toluene was stirred at 60° C. for 2 hrs. It was evaporated to dryness to give 34 g crude product which was crystallized from hexane, m.p. 75°-6° C.

EXAMPLE 8

2-Cyano-2-[1,3-dihydro-(1,4)-benzothiazine-2-ilidene]acetamide

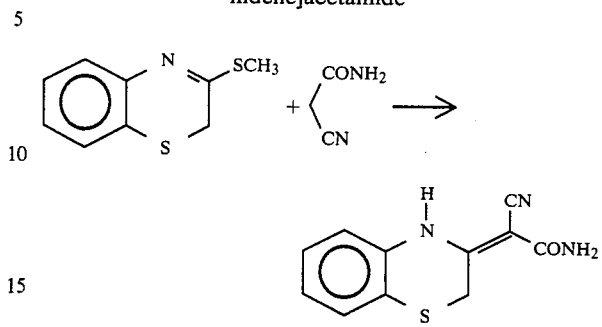

To a mixture of 0.5 g NaH in 20 ml dry DMF was first added 1.8 g cyanoacetamide and then after ½ hr. 4 g of 2-methylthio-3(H)-(1,4)benzothiazine and stirring was continued at 70° C. for 16 hrs. It was poured on ice-water, filtered giving 3.5 g crude product which on crystallization with DMF/H₂O gave 2.2 g, m.p. 264°-6° C.

EXAMPLE 9

2-Cyano-2-[1,3-dihydro-(1,4)benzothiazine-2-ilidene]acetonitrite

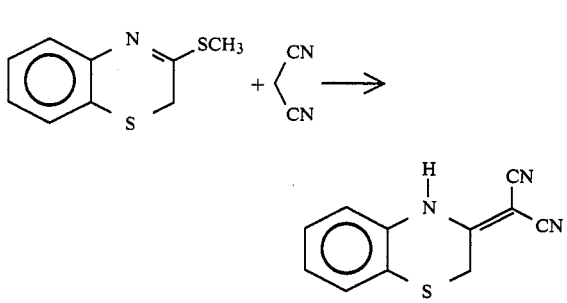

To a mixture of 0.6 g NaH in 30 ml DMF was first added 2.1 g malononitrite and then after 1 hr. 5 g of 2-methylthio-3(H)-(1,4)benzothiazine and stirring was continued at 70° C. for 20 hrs. It was poured on ice-water and extracted with hexane. The aqueous solution was acidified with HOAc and filtered to give 1.2 g crude product which was crystallized from acetonitrile/water giving 0.7 g; m.p. 253°-5° C.

EXAMPLE 10

Diethyl-2[1,3-dihydro-4,4-dioxo-(1,4)benzathiazine-2-ilidene]malonate

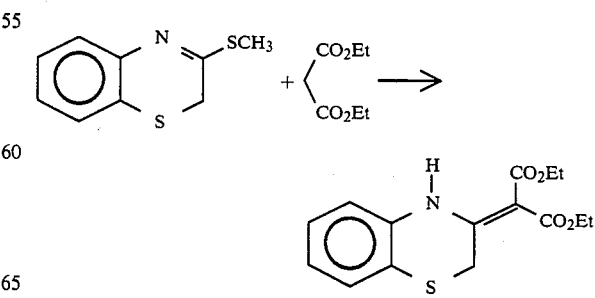

To a cold mixture of 0.5 g NaH in 20 ml dry DMF was first added 3.2 g diethyl malonate and then after 1 hr. 4.4 g 2-methylthio-4,4-dioxo-3(H)-(1,4)benzothiazine and stirring was continued at 60° C. for 18 hrs. It was then poured on ice-water, filtered giving 2.1 g crude product which was crystallized with acetonitrile-hexane to give 1.1 g product.

EXAMPLE 11

Ethyl-2-chloro-2-[1,3 dihydro-(1,4)-benzothiazine-2-ilidene]acetate

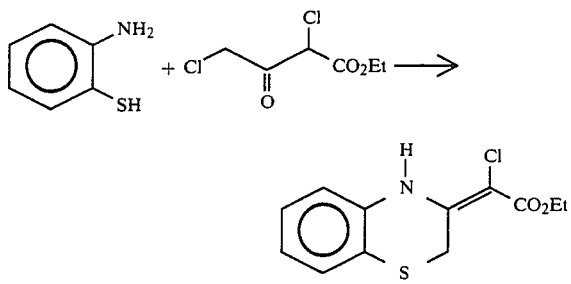

To an ice cold mixture of 0.9 g NaHCO₃ in 30 ml isopropanol and 30 ml water was first added 1.25 g of 2-aminothiophenol and then after ½ hr. 2 g of 2,4-dichloroacetoacetate (Lonzo Chemical Co.) and stirring was continued for 4 hrs. After filtration, the crude solid product was crystallized from EtOAc/hexane giving 1.7 g, m.p. 128°-9° C.

EXAMPLE 12

Ethyl-2-chloro-2-[1,3-dihydro-pyrido(2,3-b)(1,4)thiazine-2-ilidene]acetate

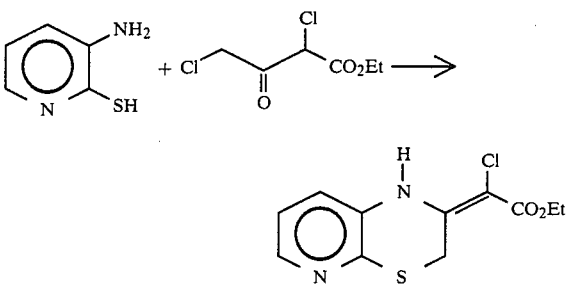

To an ice cold solution of 1.3 g 3-amino-2-mercaptopyridine and 0.9 g NaHCO₃ in 50 ml isopropanol and 50 ml water was slowly added 2 g of ethyl-2,4-dichloroacetoacetate and stirring was continued for 4 hrs. It was then diluted with water and filtered. The crude solid product was crystallized from EtOAc to give 1.7 g, m.p. 153°-5° C.

EXAMPLE 13

Ethyl-2[1,3-dihydro-(1,4)benzothiazine-2-ilidene]-2-(N-diazodiethyl-carbonyl)-acetate

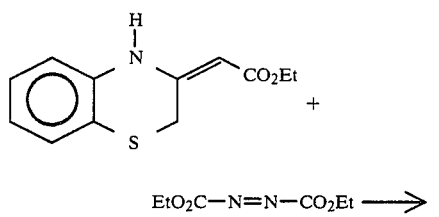

EtO₂C—N=N—CO₂Et ⟶

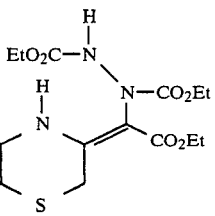

A mixture of 2.4 g of ethyl-2-[1,3-dihydro-[1,4]benzothiazine-2-ilidene]acetate, 3 g diethylazadicarboxylate in 50 ml toluene was stirred at 90° C. for 4 hrs. It was evaporated to dryness, dissolved in EtOAc, treated with Norite and filtered. After removal of the solvent, the crude product was crystallized from chloroform-hexane to give 1.3 g, m.p. 169°-71° C.

EXAMPLE 14

N-Phenyl-2-[1,3 dihydro-(1,4)benzothiazine-2-ilidene](N-diazodiethoxycarbonyl)-acetamide

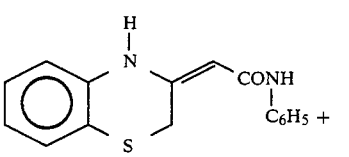

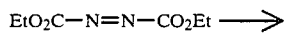

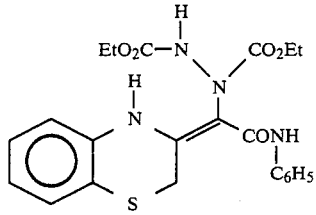

A mixture of 5.6 g of N-phenyl-2[1,3-dihydro-[1,4]benzothiazine-2-ilidene]acetamide, 6 g of diethylazodicarboxylate in 150 ml toluene was stirred at 70° C. for 4 hrs. It was filtered, washed with toluene giving 8.1 g product, m.p. 207°-10° C. which was crystallized from ethylacetate-hexane, m.p. 208°-10° C.

EXAMPLE 15

Ethyl-1,2-dioxo-pyrolo[2,1-c][1,4]benzothiazine-3-carboxylate

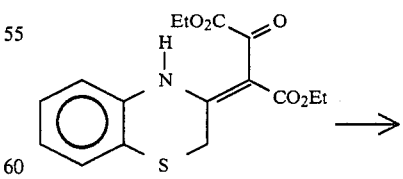

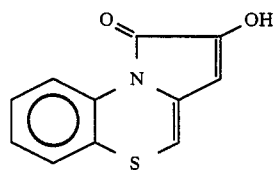

A solution of 15 g of diethyl-2-[1,3-dihydro-[1,4]benzothiazine-2-ilidene]-3-oxo-succinate in 100 ml ethanolic HCl was stirred at 100° C. for 1 hr. It was cooled, filtered, and washed with ethanol. The crude solid product was crystallized from hot ethanol to give 7.9 g, m.p. 172°-3° C.

EXAMPLE 16

3-Carbomethoxy-4-Carbethoxy-1-oxo-pyrido[2,1-C][1,4]benzothiazine

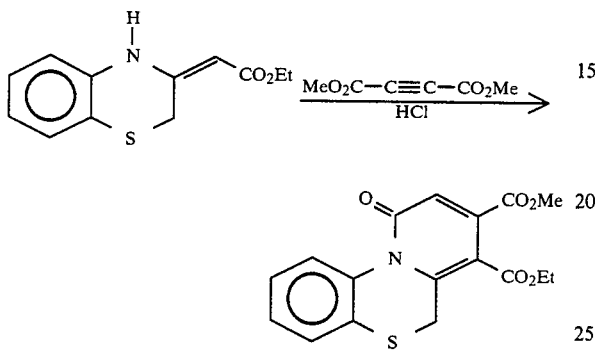

To a solution of 5 g of ethyl-2-[1,3-dihydro-[1,4]-benzothiazine-2-ilidene]acetate in 13 ml glacial HOAc and 400 ml methanol was added 20 g dimethylacetylene dicarboxylate and stirred was continued at reflux for 2 hrs and then at R.T. for 16 hrs. It was evaporated to dryness, dissolved in EtOAc, washed with NaHCO₃ and H₂O, dried over MgSO₄ and concentrated. The crude mixture was purified by HPLC using 10% EtOAc-hexane as eluent giving 2.4 g product, m.p. 143°-4° C.

EXAMPLE 17

1-Oxo-pyrido[2,1-C][1.4]benzothiazine-3,4-dicarboxylic acid

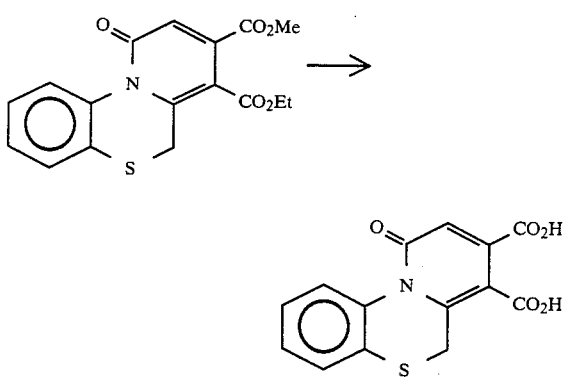

A mixture of 12 g of 3-carbomethoxy-4-carbethoxy-1-oxo-pyrido[2,1-C][1,4]benzothiazine in 270 ml 0.5N NaOH and 60 ml ethanol was stirred at 60° C. for 2 hrs. It was then acidified with 1N HCl, filtered, the precipitate washed with water and dried to give 8.5 g crude solid which was purified by dissolving in 1N NaOH and crystallizing out by addition of 1N HCl. It was then filtered, washed with water and ether to give 7.8 g product, m.p. 222° C. (decomposition).

EXAMPLE 18

1-oxo-pyrido[2,1-C][1,4]benzothiazine-3-carboxylic acid

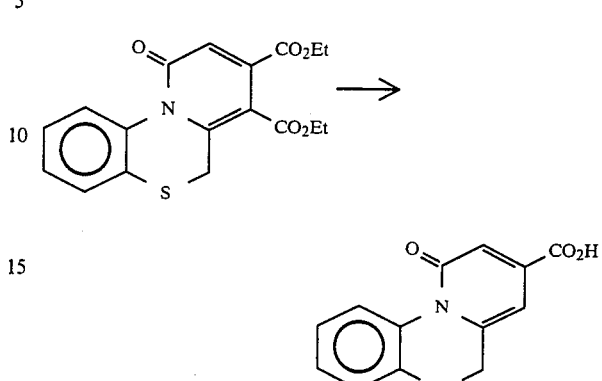

A mixture of 6 g of 1-oxo-pyrido[2,1-C][1,4]benzothiazine-3,4-dicarboxylic acid in 60 ml Dow-Therm-A was stirred at 230° C. for 1 hr. (until no more gas was evolved). It was then allowed to cool, filtered, and the precipitate washed with ether giving 4.1 g crude product which was crystallized from 1N NaOH and 1N HCl to give 3.5 g product, m.p. 222° C.

The compounds of the present invention have potent activity in regulating the action of lipoxygenase and as such possess therapeutic value in the treatment of inflammatory conditions and allergic responses such as anaphylaxis and asthma.

Lipoxygenases in mammals have been found in the lung, platelets, and white cells. They are enzymes capable of oxidizing arachidonic acid into hydroperoxyeicosatetraenoic acids (HPETEs) and their stable products hydroxyeicosatetraenoic acids (HETEs). Lipoxygenases are classified according to the position in the arachidonic acid which is oxygenated. Platelets metabolize arachidonic acid to 12-HETE, while polymorphonuclear leukocytes contain 5 and 15 lipoxygenases. It is known that 12-HETE and 5,12-diHETE are chemotactic for human neutrophils and eosinophils, and may augment the inflammation process. 5-HPETE is known to be a precursor of slow-reacting substance of anaphylaxis (SRS-A). The SRS family of molecules, such as leukotrienes B, C, and D, have been shown to be potent bronchoconstrictors (see, NATURE 288, 484-486 (1980)).

The following protocol describes an assay to detect inhibitors of the lipoxygenase pathway. Such inhibitors are believed to be capable of modulating the biosynthesis of the leukotrienes, a property believed to be useful in treating asthma and inflammatory disease states.

Protocol for Detecting Inhibitors of the Lipoxygenase Pathway (LOX)

A suspension of rat neutrophils in buffer is incubated for 3 minutes at 30° C. with [$^{14}$C]-arachidonic acid (AA) and Calcium Ionophore A23187. Citric Acid (2M) is used to quench the reaction. Following the addition of a trace amount of ($^3$H)-5-HETE together with an excess of unlabeled 5-HETE to each tube, the mixture is extracted with chloroform/methanol. The organic layer is washed with dilute acid and an aliquot is transferred to glass tubes and dried. The residue is dissolved in a small volume of chloroform and an aliquot is spotted on silica gel TLC sheets, which are developed with an ethyl acetate/isoctane/water/acetic acid solvent system. The 5-HETE spots are visualized with iodine, cut out and placed in scintillation vials for counting. After adjusting for the extraction efficiency, the amount (pmole) of [$^{14}$C]-5-HETE in each of the tubes is quantitated. The net pmoles of 5-HETE are obtained by substracting the pmoles of 5-HETE in the tubes containing buffer alone (blank) for the pmoles of 5-HETE in the tubes containing buffer and cells (control). The ability of the test compounds to modulate the activity of this enzyme is determined by a decrease or increase in the net amount of 5-HETE produced.

Table I—(LOX column) shows the concentration required for 50% inhibition of the 5-lipoxygenase pathway (5-LOX/$I_{50}$ uM) or degree of activity for representative compounds according to the present invention.

Leukotrienes, the products of the 5-lipoxygenase pathway of arachidonic acid metabolism, are potent contractile agents with a variety of smooth muscle preparations. Thus, it has been hypothesized that the leukotrienes contribute significantly to the pathophysiology of asthma. The following protocol describes an in vitro assay used to test compounds which specifically antagonize the actions of leukotrienes.

Protocol for SRS-A (slow-reacting substance of anaphylaxis) Antagonists (SRS-A)

Peripheral strips of guinea pig lungs are prepared and hung in tissue baths (Metro # ME-5505, 10 ml) according to the published procedure (Proc. Nat'l Acad. Sci, U.S.A. Volume 77, pp. 4354–4358, 1980). The strips are thoroughly rinsed in Assay Buffer and then connected with surgical silk thread to the support rods from the tissue baths. The rods are adjusted in the baths and the strips connected to the pressure transducers (Grass FT 103 or Gould UC-3). The tissue baths are aerated with 95% oxygen-5% carbon dioxide and maintained at 37° C. The Assay Buffer has been made as follows: For each liter of buffer the following are added to approximately 800 ml of water distilled in glass—6.87 g. NaCl, 0.4 g. KCl, 2.1 g. NaHCO$_3$, 0.14 g, NaH$_2$PO$_4$.H$_2$O, 0.21 g. MgSO$_4$.7H$_2$O, and 2.0 g. D-glucose. Then a solution of 0.368 g. CaCl$_2$.2H$_2$O in 100 ml glass-distilled water is slowly added to the buffer. Sufficient water is added to adjust the volume to one liter, and the solution is aerated with 95% oxygen-5% carbon dioxide. Usually 10 liters of buffer are used for an experiment with 4 tissues.

After the tissues have been repeatedly washed and allowed to equilibrate in the tissue bath, they are challenged with 1 uM histamine. After maximum contractions have been obtained, the tissues are washed, and allowed to relax back to baseline tension. This histamine challenge procedure is repeated at least 1 to 2 more times to obtain a repeatable control response. The average response to 1 uM histamine for each tissue is used to normalize all other challenges.

Responses of each tissue to a pre-determined concentration of leukotriene are then obtained. Usually test compounds are examined initially at 30 uM on resting tension of the tissues without any added agonist or antagonist to determine if the compound has any possible intrinsic activity. The tissues are washed, and the test compound is added again. Leukotriene is added after the desired pre-incubation time. The intrinsic activity of the compounds, and their effect on leukotriene-induced contractions are then recorded.

The concentration required for 50% inhibition of 0.2 nM leukotriene C$_4$-induced contraction of guinea pig peripheral strips or degree of inhibitory activity for representative compounds of the present invention is shown in Table I denoted by SRS-A.

Representative compounds of the present invention were also tested in the following in vivo model.

Protocol for in vivo Testing of Modulators of SRS-A (slow reacting substances of anaphylaxis) (BAGEL)

This test, known as the Bronchial Anaphylaxis in Guinea Pigs with Enhanced Leukotrines (BAGEL), is based on the procedure published in Agents and Actions, Vol. 11, pp. 396-401, 1981, and is performed with guinea pigs actively immunized (14 days) with ovalbumin (2.7 mg/kg, i.p.) and *B.pertussis* (5 × 10$^9$ organisms) as an adjuvant. Prior to challenge with antigen (ovalbumin), the animals are anesthetized and prepared for monitoring pulmonary dynamics by whole body plethysmography. They are treated with an H$_1$ antihistamine (methapyrilene, 2 mg/kg, i.v.) and cyclooxygenase inhibitor (indomethacin; 20 mg/kg, i.p.) in order to enhance the SRS-A component of anaphylactic bronchoconstriction. Bronchoconstriction is quantified as the maximum increase in airway resistance following antigen challenge. The drug is administered either i.p. 10 minutes before challenge, or i.d. 15 minutes before challenge.

In Table I (BAGEL column) shows the results of testing a few compounds of the present invention according to this protocol.

TABLE I

| STRUCTURE | LOX $I_{50}$mM | SRS-A $I_{50}$mM | BAGEL |
|---|---|---|---|
| benzothiophene-NH derivative with CO$_2$Et | I | | M |
| benzothiophene-NH derivative with CONHC$_6$H$_5$ | 1.6 | | 18 |

TABLE I-continued

| STRUCTURE | LOX I$_{50}$mM | SRS-A I$_{50}$mM | BAGEL |
|---|---|---|---|
| 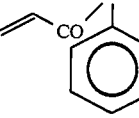 | M | T | |
| 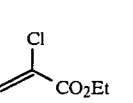 | 1.7 | M | (L) at 200 mg/kg i.d. |
| 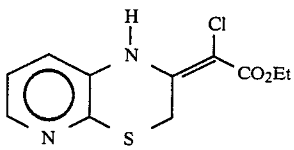 | 1.2 (Human PMN 1μ.M) | 20 | (M-H) at 200 mg/kg i.d. |
| 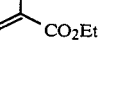 | I | 25 | |
| 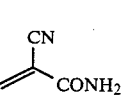 | 3μ.M (Human PMN L(135μ M) | I | (H) at 30 mg/Kg i.d. |
| 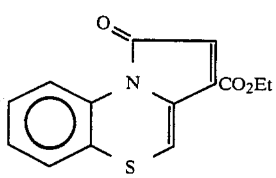 | 12 | I | 200 mg/Kg i.d. |

Abbreviations in Table I denote the following:
I = inactive
L = low activity
M = moderate activity
H = high activity As can be readily ascertained from the foregoing, the compounds of the present invention are effective in inhibiting the interactions of antibodies and cells believed to participate in causing allergic reactions, as well as inhibiting the allergic secretion of histamine from histamine-containing cells. As such, the compound of the present invention may be used in preventive treatment of the human or animal body and in combating diseases, in particular several forms of allergic and asthmatic diseases, specifically asthma bronchial, allergic bronchitis, asthmatic bronchitis, food allergy, hay fever allergic rhinitis and allergic conjunctivitis.

Having described the invention, it will be apparent to one of ordinary skill in the art that changes and modifications can be made thereto without departing from the spirit and scope of the invention as set forth herein.

What is claimed is:

1. A member of the formulae:

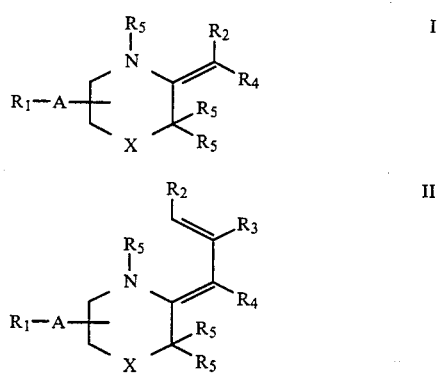

-continued

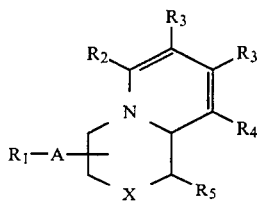
III wherein,
A is benzo or pyrido;
X is S;
$R_1$ is H, $C_1$-$C_6$ alkyl, OH, OR, halogen, nitro, COOR,

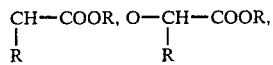

wherein R in OR, COOR,

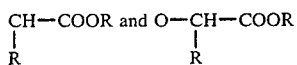

denotes lower alkyl having 1 to 6 carbon atoms;
$R_2$, $R_3$, $R_4$ and $R_5$ are identical or different and each represent H, $C_1$-$C_6$ alkyl, OH, OR, cyano, halogen, or COOR, wherein R in OR and COOR denotes lower alkyl having 1 to 6 carbon atoms; and pharmaceutically acceptable salts thereof.

2. The compound of claim 1 wherein said halogen is Cl, F or Br.

3. An anti-allergic or anti-inflammatory composition comprising an anti-allergic or anti-inflammatory effective amount of a member of the formulae:

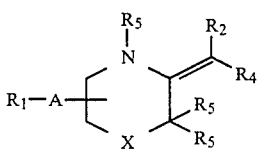
I

-continued

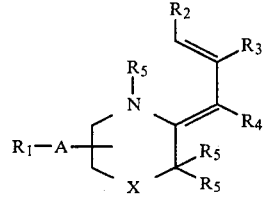
II

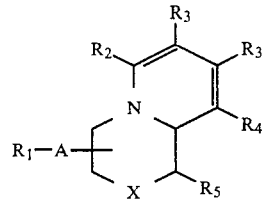
III wherein,
A is benzo or pyrido;
X is S;
$R_1$ is H, $C_1$-$C_6$ alkyl, OH, OR, halogen, nitro, COOR,

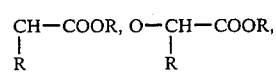

wherein R in OR, COOR,

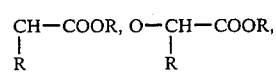

denotes lower alkyl having 1 to 6 carbon atoms;
$R_2$, $R_3$, $R_4$ and $R_5$ are identical or different and each represent H, $C_1$-$C_6$ alkyl, OH, OR, cyano, halogen, or COOR, wherein R in OR and COOR denotes lower alkyl having 1 to 6 carbon atoms; and pharmaceutically acceptable salts thereof, in a pharmaceutically acceptable carrier.

4. The anti-allergic or anti-inflammatory composition of claim 3 wherein said halogen is Cl, F or Br.

5. A method of treating allergic or inflammatory conditions in a mammal comprising: administering to said mammal an anti-allergic or anti-inflammatory effective amount of the composition of claim 3 to relieve such allergic or inflammatory conditions.

* * * * *